(12) United States Patent
Strauss et al.

(10) Patent No.: US 12,252,739 B2
(45) Date of Patent: Mar. 18, 2025

(54) SELECTIVELY CONTROLLABLE CLEAVABLE LINKERS

(71) Applicant: MICROSOFT TECHNOLOGY LICENSING, LLC, Redmond, WA (US)

(72) Inventors: Karin Strauss, Seattle, WA (US); Bichlien Hoang Nguyen, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 18/156,511

(22) Filed: Jan. 19, 2023

(65) Prior Publication Data
US 2023/0151411 A1 May 18, 2023

Related U.S. Application Data

(63) Continuation of application No. 16/230,787, filed on Dec. 21, 2018, now Pat. No. 11,584,956.

(51) Int. Cl.
*C07K 1/04* (2006.01)
*C07H 21/04* (2006.01)
(Continued)

(52) U.S. Cl.
CPC .......... *C12Q 1/6834* (2013.01); *C07H 21/04* (2013.01); *C07H 99/00* (2013.01); *C07K 1/042* (2013.01);
(Continued)

(58) Field of Classification Search
CPC ........ C07H 21/00; C07H 21/02; C07H 21/04; C12Q 1/6834; C12N 2310/351; C12N 2310/3513; C07K 1/04; C07K 1/042
See application file for complete search history.

(56) References Cited

U.S. PATENT DOCUMENTS

| | | |
|---|---|---|
| 6,423,172 B1 | 7/2002 | Mcardle et al. |
| 7,056,666 B2 | 6/2006 | Dower |

(Continued)

FOREIGN PATENT DOCUMENTS

| | | | |
|---|---|---|---|
| WO | WO-9726002 A1 * | 7/1997 | ............... C07K 1/04 |
| WO | 2008051454 A1 | 5/2008 | |

(Continued)

OTHER PUBLICATIONS

Wu et al., "Molecular hydrogelators of peptoid-peptide conjugates with superior stability against enzyme digestion" Nanoscale vol. 4 pp. 3644-3646 (Year: 2012).*

(Continued)

*Primary Examiner* — Eric Olson
(74) *Attorney, Agent, or Firm* — Benjamin Keim; Newport IP, LLC

(57) ABSTRACT

Selectively controllable cleavable linkers include electrochemically-cleavable linkers, photolabile linkers, thermolabile linkers, chemically-labile linkers, and enzymatically-cleavable linkers. Selective cleavage of individual linkers may be controlled by changing local conditions. Local conditions may be changed by activating electrodes in proximity to the linkers, exposing the linkers to light, heating the linkers, or applying chemicals. Selective cleaving of enzymatically-cleavable linkers may be controlled by designing the sequences of different sets of the individual linkers to respond to different enzymes. Cleavable linkers may be used to attach polymers to a solid substrate. Selective cleavage of the linkers enables release of specific polymers from the solid substrate. Cleavable linkers may also be used to attach protecting groups to the ends of growing polymers. The protecting groups may be selectively removed by cleavage of the linkers to enable growth of specific polymers.

9 Claims, 6 Drawing Sheets

(51) Int. Cl.
*C07H 99/00* (2006.01)
*C07K 1/10* (2006.01)
*C07K 14/00* (2006.01)
*C07K 17/00* (2006.01)
*C07K 17/02* (2006.01)
*C07K 17/08* (2006.01)
*C07K 19/00* (2006.01)
*C12Q 1/6834* (2018.01)

(52) U.S. Cl.
CPC .............. *C07K 1/045* (2013.01); *C07K 1/047* (2013.01); *C07K 1/10* (2013.01); *C07K 14/003* (2013.01); *C07K 17/00* (2013.01); *C07K 17/02* (2013.01); *C07K 17/08* (2013.01); *C07K 19/00* (2013.01); *B01J 2219/00454* (2013.01); *B01J 2219/00603* (2013.01); *B01J 2219/00626* (2013.01); *B01J 2219/00653* (2013.01); *C07K 2319/02* (2013.01); *C12N 2310/351* (2013.01); *C12N 2310/3513* (2013.01)

(56) References Cited

U.S. PATENT DOCUMENTS

| | | |
|---|---|---|
| 2006/0046262 A1 | 3/2006 | Mauritz |
| 2011/0092384 A1* | 4/2011 | Kwon .................. C07K 7/64 530/323 |
| 2012/0029056 A1 | 2/2012 | Alevizos et al. |
| 2019/0113521 A1* | 4/2019 | Moola .................. C40B 30/04 |
| 2021/0238577 A1 | 8/2021 | Nguyen et al. |
| 2022/0362734 A1 | 11/2022 | Nguyen et al. |
| 2023/0348946 A1 | 11/2023 | Nguyen |

FOREIGN PATENT DOCUMENTS

| | | | |
|---|---|---|---|
| WO | WO-2017165438 A1 * | 9/2017 | .......... B01J 19/0046 |
| WO | 2020131588 A1 | 6/2020 | |
| WO | 2020247090 A1 | 12/2020 | |

OTHER PUBLICATIONS

"Non-Final Office Action Issued in U.S. Appl. No. 17/815,380", Mailed Date: Dec. 1, 2023, 9 Pages.
"Notice of Allowance Issued in U.S. Appl. No. 16/597,799", Mailed Date: Sep. 29, 2023, 9 Pages.
"Final Office Action Issued in U.S. Appl. No. 16/435,363", Mailed Date: Nov. 7, 2023, 16 Pages.
"Notice of Allowance Issued in U.S. Appl. No. 16/543,433", Mailed Date: Feb. 8, 2023, 8 Pages.
"Final Office Action Issued in U.S. Appl. No. 17/695,734", Mailed Date: Feb. 9, 2023, 9 Pages.
"International Search Report and Written Opinion Issued in PCT Application No. PCT/US22/042409", Mailed Date: Feb. 23, 2023, 9 Pages.
"Non Final Office Action Issued in U.S. Appl. No. 16/435,363", Mailed Date: Mar. 8, 2023, 10 Pages.
"Notice of Allowance Issued in U.S. Appl. No. 16/543,433", Mailed Date: Mar. 29, 2023, 7 Pages.
"Non Final Office Action Issued in U.S. Appl. No. 17/815,380", Mailed Date: Mar. 9, 2023, 8 Pages.
Kim, et al., "Hierarchical gene synthesis using DNA microchip oligonucleotides", In Journal of Biotechnology, vol. 151, Issue 4, Feb. 20, 2011, pp. 319-324.
"Notice of Allowance Issued in U.S. Appl. No. 16/543,433", Mailed Date: Apr. 14, 2023, 6 Pages.
"Non Final Office Action Issued in U.S. Appl. No. 16/597,799", Mailed Date: Apr. 6, 2023, 7 Pages.
US-2022-0023820, Jan. 27, 2022.
US-2020-0384434, Dec. 10, 2020.
US-2021-0047669, Feb. 18, 2021.
Corrected Notice of Allowability mailed on May 3, 2024, in U.S. Appl. No. 17/815,380, 7 pages.
Notice of Allowance mailed on May 30, 2024, in U.S. Appl. No. 17/695,734, 08 pages.
Notice of Allowance mailed on Apr. 3, 2024, in U.S. Appl. No. 17/815,380, 9 pages.
Communication pursuant to Article 94(3) received in European Application No. 19842441.8, mailed on Oct. 16, 2024, 8 pages.
Communication pursuant to Article 94(3) Received in European Patent Application No 20725319.6, mailed on Sep. 24, 2024, 4 pages.
Langston, Jennifer, "UW, Microsoft researchers break record for DNA data storage", Retrieved from the URL: https://www.washington.edu/news/2016/07/07/uw-microsoftresearchers-break-record-for-dna-data-storage/, Jul. 7, 2016, 5 Pages.
Egeland, et al., "An Electrochemical Redox Couple Activated by Microelectrodes for Confined Chemical Patterning of Surfaces" Analytical Chemistry, vol. 74, 2002, pp. 1590-1596.
Non-Final Office Action mailed on Dec. 12, 2024, in U.S. Appl. No. 17/494,320, 18 pages.
Notice of allowance mailed on Dec. 16, 2024, in U.S. Appl. No. 16/435,363, 7 pages.
Communication pursuant to Article 94(3) Received in European Patent Application No. 20792779.9, mailed on Nov. 19, 2024, 4 pages.
Final Office Action mailed on Dec. 30, 2024, in U.S. Appl. No. 18/221,364, 10 pages.

* cited by examiner

SELECTIVELY CONTROLLABLE CLEAVABLE LINKERS

CROSS-REFERENCE TO RELATED APPLICATION

This application is a continuation of U.S. patent application Ser. No. 16/230,787, filed Dec. 21, 2018, the content of which application is hereby expressly incorporated herein by reference in its entirety.

BACKGROUND

Linkers are used for many applications in biotechnology. Oligonucleotides and peptides are attached to solid supports during solid-phase synthesis with linkers. These types of linkers are typically cleaved by washing the solid support with a strong acid or base solution. Linkers may also be used to attach protecting groups that control the polymerization of oligonucleotides and polypeptides. An acid or base solution is also typically used to remove protecting groups.

Cleavage of linkers using chemicals such as acids and bases creates chemical waste and may require the use of specialized equipment. These techniques for cleaving linkers are nonspecific and generally cleave all linkers present. There is also the potential for cross-reactions between the chemicals used to cleave linkers and the oligonucleotides, polypeptides, or other molecules attached to a linker.

SUMMARY

This disclosure provides multiple techniques and linker designs for achieving selective cleavage of linkers. Selective control of linker cleavage allows for less than all the linkers present in a given system to be cleaved. This makes it possible to release some but not all of the molecules attached to a solid support. It also allows for fine-grain control of protecting group removal and subsequent polymer growth.

Linkers attached to a solid support, or substrate, may be selectively activated by controlling local conditions on a portion of the substrate. Local conditions may be controlled by changing the substrate such as by selectively activating electrodes on a microelectrode array. Precise application of heat such as by use of resistors integrated into an array may be used to selectively cleave thermolabile linkers. Lithography techniques may be used to selectively expose photolabile linkers to light. Chemical cleaving agents may also be applied to selected linkers through the use of precise application techniques such as, but not limited to, chemical inkjet printing. Thus, out of a large number of linkers having the same or similar chemical structure, a selected subset may be cleaved by changing the local conditions for only those linkers.

Linkers may also be selectively cleaved by enzymes that recognize specific linker sequences. Linkers may be made out of oligonucleotides or polypeptides which are subject to sequence-specific cleavage by enzymes such as restriction endonucleases and peptidases. A set of linkers, such as linkers on a solid support structure, may include different sets of linkers each having a different sequence that is recognized by a different enzyme. Selective cleavage is achieved by exposing the linkers to the specific enzyme which will cleave only those linkers having a sequence recognized by the specific enzyme.

Selectively-cleavable linkers may be used in any number of different types of applications such as attaching molecules to a substrate or attaching a protecting group to the end of a growing polymer. When used as "surface linkers" for attaching molecules to a substrate, selectively controlling the cleavage of the linkers allows for selective release of the attached molecules. When used as "chain linkers" for attachment of a protecting group, selectively controlling the cleavage of the linkers allows for selection of specific molecules to be unprotected and modified. Use of selectively-cleavable linkers such as electrochemically-cleavable linkers, thermolabile linkers, or photolabile linkers provides controllable linkers without creating chemical waste or cross-reactions with molecules attached to the linkers.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
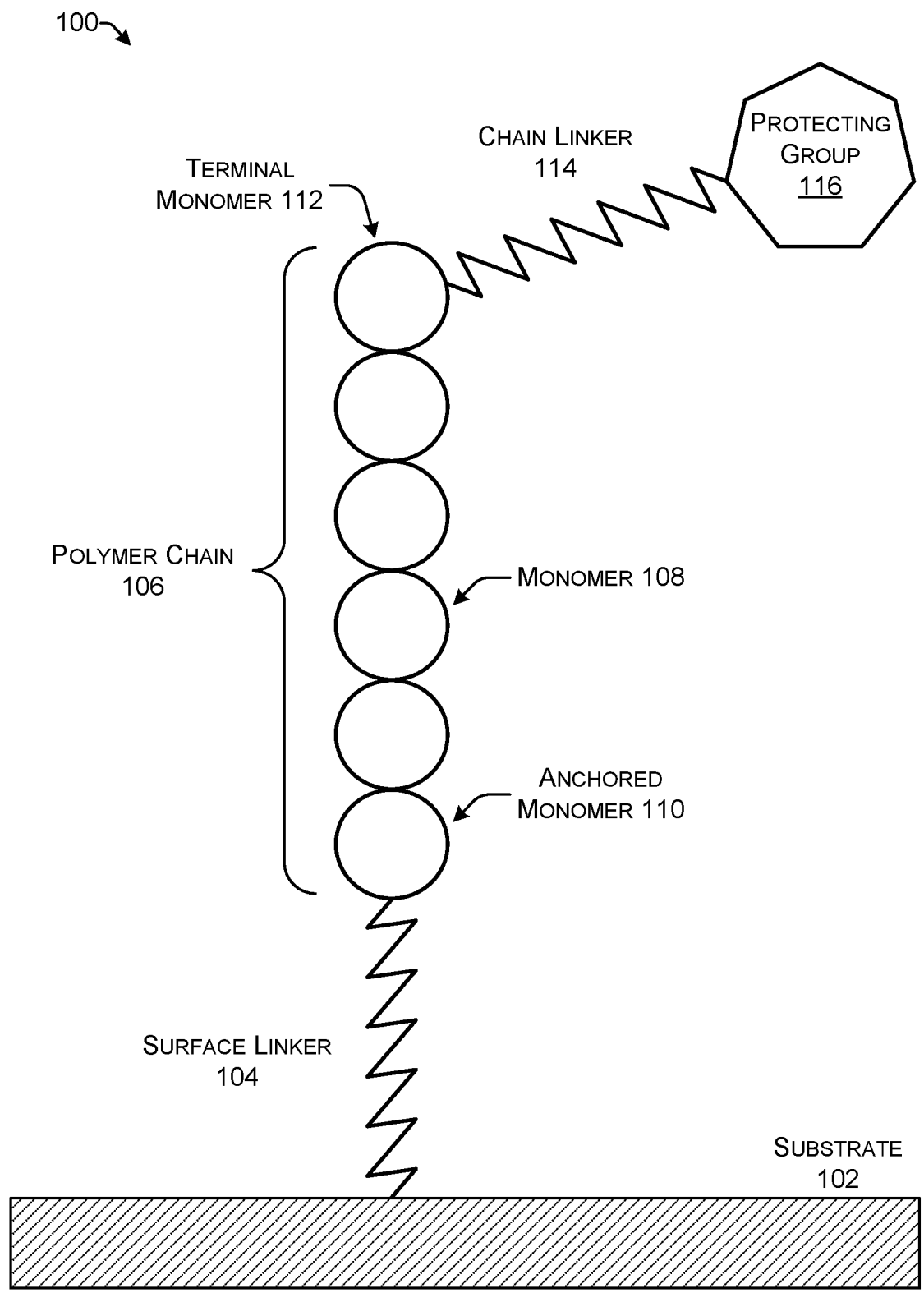
FIG. 1 illustrates a polymer connected to a substrate by a first linker and connected to a protecting group by a second linker.

One application for the use of linkers is de novo synthesis of oligonucleotides. Oligonucleotides include both deoxyribose nucleic acid (DNA), ribonucleic acid (RNA), and hybrids containing mixtures of DNA and RNA. DNA includes nucleotides with one of the four natural bases cytosine (C), guanine (G), adenine (A), or thymine (T) as well as unnatural bases, noncanonical bases, and modified bases. RNA includes nucleotides with one of the four natural bases cytosine, guanine, adenine, or uracil (U) as well as unnatural bases, noncanonical bases, and modified bases.

Currently, de novo synthesis of oligonucleotides is most commonly implemented as solid-phase synthesis using the phosphoramidite method which combines phosphoramidite building blocks in the presence of a tetrazole catalyst. Nucleoside phosphoramidites are derivatives of natural or synthetic nucleosides. A phosphoramidite is a normal nucleotide with protecting groups, such as a trityl group, added to its reactive amine, hydroxyl, and phosphate groups. These protecting groups prevent unwanted side reactions and force the formation of the desired product during synthesis. Synthesis begins with a single phosphoramidite tethered to a solid support by a linker such as a succinyl linker coupled to a long chain alkylamine spacer.

The phosphoramidite method uses a cycle of four different chemistry mixtures to add each individual nucleoside in a 3' to 5' synthesis direction. First, a dimethoxytrityl (DMT)-protected nucleoside phosphoramidite that is attached to a solid support is deprotected by removal of the DMT using trichloroacetic acid (TCA) in a deblocking step. This reveals a free 5'-hydroxyl group. Second, in an activation step a new DMT-protected phosphoramidite is coupled to the 5'-hydroxyl group of the growing oligonucleotide chain to form a phosphite triester. Third, a capping step acetylates any remaining unreacted 5' hydroxyl groups, making the unreacted oligonucleotide chains inert to further nucleoside additions and preventing one source of base deletions. Capping is accomplished by adding an acetylating reagent composed of acetic anhydride and N-methyl imidazole. This reagent reacts only with free hydroxyl groups to irreversibly cap the oligonucleotides in which coupling failed. Fourth, an iodine oxidation converts the phosphite to a phosphate, producing a cyanoethyl-protected phosphate backbone stabilizing the phosphate linkage between the monomers in the growing oligonucleotide chain. The DMT protecting group is removed to allow the cycle to continue and add the next nucleoside.

The protection of the exocyclic amino groups on adenine, cytosine, and guanine has to be orthogonal to that of the 5'-hydroxy group because the DMT is removed at the end of each synthetic cycle. One technique is to use base-labile protecting groups on the exocyclic amino groups to create orthogonality with the TCA cleavage of the DMT protecting group.

After synthesis is complete, all the protecting groups are removed and the single-stranded oligonucleotide is cleaved from the solid support. Coupling to the solid support is achieved by covalently attaching non-nucleoside linkers to reactive amino groups on the surface of the solid support. A phosphoramidite respective to the 3'-terminal nucleoside residue is coupled to the linker in the first synthetic cycle of oligonucleotide chain assembly using the standard protocols. These non-nucleoside linkers are typically cleaved by using a mixture of bases such as gaseous ammonia, aqueous ammonium hydroxide, and aqueous methylamine.

Solid-phase synthesis of peptides (SPSS) is another application for the use of linkers. Peptide synthesis is the production of peptides, compounds where multiple amino acids are linked via amide bonds, also known as peptide bonds. Amino acids as used herein includes all 20 standard amino acids, all 22 natural amino acids, non-proteinogenic amino acids, and D-isomers. Peptides are chemically synthesized by the condensation reaction of the carboxyl group of one amino acid to the amino group of another. Protecting group strategies are usually necessary to prevent undesirable side reactions with the various amino acid side chains. Chemical peptide synthesis most commonly starts at the carboxyl end of the peptide (C-terminus) and proceeds toward the amino-terminus (N-terminus).

SPPS allows the rapid assembly of a peptide chain through successive reactions of amino acid derivatives on an insoluble porous support. The general SPPS procedure is one of repeated cycles of alternate N-terminal deprotection and coupling reactions. First, an amino acid is linked to the solid support with a covalent bond between the carbonyl group of the amino acid and solid support. The bond coupling the amino acid to the solid support may be an amido or an ester bond. Subsequently, the amine is deprotected and then coupled with the free acid of the second amino acid. This cycle repeats until the desired sequence has been synthesized. SPPS cycles may also include capping steps which block the ends of unreacted amino acids from reacting. The protecting groups for the amino groups used in peptide synthesis are fluorenylmethyloxycarbonyl group (Fmoc) and tert-butyloxycarbonyl (Boc). Reactive side chains of amino acids are also protected with protecting groups that are orthogonal to the protecting group used for the amino group. At the end of the synthesis, the peptide is cleaved from the solid support while simultaneously removing all protecting groups using a strong acid such as trifluoroacetic acid or a nucleophile.

The Fmoc protecting group is base-labile. It may be removed with a dilute base such as piperidine. If Fmoc is used, the site-chain protecting groups may be provided by ester, ether and urethane derivatives of tert-butanol. These side-chain protecting groups are removed by treatment with trifluoroacetic acid (TFA), which also cleaves the bond anchoring the peptide to the solid support. The Boc protecting group is removed with a mild acid (usually dilute TFA). The side-chain protecting groups used with Boc may be ester, ether, and urethane derivatives of benzyl alcohol. Hydrofluoric acid (HF) can be used both to deprotect the amino acid side chains and to cleave the peptide from the resin support.

This disclosure provides techniques and structures for selectively-cleavable linkers that can be used with oligonucleotide synthesis, DNA sequencing-by-synthesis, polypeptide synthesis, and other biochemical processes. Additional illustrative applications for selectively-cleavable linkers exist in fields such as DNA origami and DNA data storage.

DNA origami is the nanoscale folding of DNA to create non-arbitrary two- and three-dimensional shapes at the nanoscale. The specificity of the interactions between complementary base pairs (bp) makes DNA a useful construction material, through the design of its base sequences. Short segments of DNA called "staples" hybridize to longer strands of DNA and change the shape of the longer strands. Selectively cleavable linkers made of oligonucleotides, or other material, can be used to precisely control the separation of structures made through DNA origami. For example, individual staples may be controllably released by including a selectively cleavable linker within a staple.

DNA data storage uses pools of synthetic oligonucleotides to encode digital information from computer files. The sequence of nucleotides on strands of DNA encode the zeros and ones representing any type of digital information. Oligonucleotide synthesis is used to create the strands of DNA for data storage. Selectively-cleavable linkers can control the release of newly-synthesized DNA strands from a solid support in a way that corresponds to the digital information encoded by the DNA strands. For example, all the DNA strands that contain digital information from the same computer file may be released from the solid support together and processed together. Other DNA strands that are attached to the same solid support may be retained and released later. There are numerous other applications for selectively cleavable controllable linkers FIG. 1 shows an illustrative diagram 100 of substrate 102 on which a surface linker 104 and polymer chain 106 are attached. The polymer chain 106 may be an oligonucleotide, polypeptide, or other polymer. An individual monomer 108 of the polymer chain 106 is an individual unit of the polymer such as a nucleotide or amino acid. The monomer directly connected to the surface linker 104 is referred to as an anchored monomer 110. The anchored monomer 110 may have a covalent connection to the surface linker 104. In some implementations, the anchored monomer 110 may have a covalent connection directly to the substrate 102. In these implementations the covalent bond itself is the surface linker 104.

The monomer of the polymer chain 106 that is farthest from the substrate 102 is referred to as the terminal monomer 112. If there is only one monomer attached to the surface linker 104, that single monomer is both the anchored monomer 110 and the terminal monomer 112. The terminal monomer 112 may have an attached chain linker 114 connected to a protecting group 116. The protecting group 116 may prevent elongation of the polymer chain. Thus, removal of the protecting group 116 may be part of each cycle of polymer extensions. Additionally or alternatively, the protecting group 116 may protect reactive groups on individual monomers such as amine, hydroxyl, and phosphate groups. A monomer 108 may have protecting groups 116 that both prevent elongation of the polymer and the protect reactive groups. If two types of protective groups are present on the monomers of a polymer chain 106 they may be orthogonal to each other so that removal of a protecting group 116 that prevents chain extension will not remove a separate protecting group 116 that protect reactive groups on one or more of the monomers 108.

Although the diagram 100 shows both a surface linker 104 and a chain linker 114 in implementations there may be only a surface linker 104 or only a chain linker 114. For example, a polymer chain 106 may be bound to the substrate 102 with a surface linker 104 without a protecting group 116 or a chain linker 114. Alternatively, a polymer chain 106 in solution may have a chain linker 114 and protecting group 116 attached without a covalent connection to the substrate 102.

Both the surface linker 104 and the chain linker 114 may be electrochemically-cleavable linkers, thermolabile linkers, photolabile linkers, chemically-liable linkers, or enzymatically-cleavable linkers. The surface linker 104 and the chain linker 114 both the present may be different types of linkers. In an implementation this is preferable to create orthogonality between the connection to the substrate 102 and the connection to the protecting group 116. One technique for creating orthogonality between the surface linker 104 and the chain linker 114 is to have each type of linker cleaved at a different pH. For example, the surface linker 104 may cleave at a basic pH while the chain linker 114 may cleave at an acidic pH.

Electrochemically-cleavable linkers are cleaved by addition of electrons to a bond in the linker. The electrons may be generated by activating an electrode in the proximity of the bond in the linker that is to be cleaved. This may be referred to as a "directly mediated cleavage" in which activation of the electrode, or other change in the local environment, directly causes cleavage of a bond in the linker. Electrochemically-cleavable linkers may include an ester or an amide linkage and a protected alcohol or amine that when released can trigger an inter-molecular cyclization reaction onto the ester or amide to form a lactone or lactam, thereby cleaving the linker and generating a leaving group. Illustrative examples of electrochemically-cleavable linkers are provided in FIGS. 3-6.

Thermolabile linkers are cleaved in the presence of heat. One structure that may be used to form thermolabile linkers is thermolytic hydroxyl protecting groups derived from 2-aminopyridine and its analogs. The resulting 2-pyridyl-substituted hydroxyl protecting groups can be efficiently cleaved with brief heat treatment at about 40-100° C. One example of thermolabile linkers is provided in U.S. Pat. No. 7,612,197. Another example of thermolabile linkers are linkers used in the CleanAmp™ phosphoramidite monomers available from Glen Research (Sterling, VA). The CleanAmp™ monomers have a (4-oxo-tetradecyl)-(N,N-diisopropyl)-phosphoramidite linker located at the three prime hydroxyl group of a deoxyribose sugar.

Photolabile linkers are cleaved by a specific wavelength of light corresponding to the linker chemistry. There are a large number of known types of photo-cleavable bonds. Common classes of photolabile linkers include nitrobenzyl-based linkers, benzyl nitrile-based linkers, benzyl-based linkers, and carbonyl-based linkers. Amine-to-thiol cross-linkers are also photolabile and may be lengthened by attachment to a polyethylene glycol (PEG) chain. Amine-to-thiol bonds may be cleaved by ultraviolet (UV) light with a wavelength of about 365-405 nm. The list of functional groups that can be protected include, but are not limited to, phosphates, carboxylates, carbonates, carbamates, thiolates, phenolates, and alkoxides. Additionally, while the rate varies with a number of variables, including choice of solvent and pH, the photodeprotection is possible in both solution and in with linkers bound to a substrate 102.

One type of photolabile linker uses a UV photo-cleavable C3 spacer arm that includes a nitrobenzene sidechain. Cleavage occurs by irradiation with UV light (300-350 nm). Other examples of photolabile linkers are PC Biotin Phosphoramidite with the formula 1-[2-Nitro (6-(N-(4,4'-dimethoxytrityl))-biotinamidocaproamidomethyl)phenyl]-ethyl-[2-cyanoethyl-(N,N-diisopropyl)]-phosphoramidite, PC Amino-Modifier Phosphoramidite with the formula [(6-Trifluoroacetylamidocaproamidomethyl)-1-(2-nitrophenyl)-ethyl]-2-cyanoethyl-(N,N-diisopropyl)-phosphoramidite, PC Spacer Phosphoramidite with the formula [4-(4,4'-Dimethoxytrityloxy)butyramidomethyl)-1-(2-nitrophenyl)-ethyl]-2-cyanoethyl-(N,N-diisopropyl)-phosphoramidite, and PC Linker Phosphoramidite with the formula 3-(4,4'-Dimethoxytrityl)-1-(2-nitrophenyl)-propan-1-yl-[(2-cyano-ethyl)-(N,N-diisopropyl)]-phosphoramiditen (available from Glen Research, Sterling, VA).

Chemically-labile linkers include acid-cleavable linkers and reducible linkers. Acid-cleavable linkers, such as hydrazine, cis-Aconity, and disulfide linkers, are designed to remain stable at neutral pH but undergo hydrolysis in an acidic environment. Acid-cleavable linkers generally cleaved at a pH of below about 5.0. Reducible linkers take advantage of the difference in reduction potential in basic environments. Succinic acid linker arms are used to attach oligonucleotides to solid supports are an example of reducible linkers and may be cleaved using ammonium hydroxide.

Another technique for inducing cleavage due to change in the local conditions may be referred to as "indirectly mediated cleavage." With indirectly mediated cleavage the change in the local conditions such as activation of an electrode, change in pH, change in temperature, exposure to light, addition of chemicals, etc. activates an auxiliary molecule which in turn causes cleavage of a bond in the linker. For example, the auxiliary molecule may be a photobase generator or photo acid generator into which electrons flow when exposed to photons of the appropriate wavelength that in turn releases an acid or base that cleaves a bond in the linker.

Enzymatically-cleavable linkers are cleaved by an enzyme that recognizes the specific sequence of the linker. Enzymatically-cleavable linkers may be formed from oligonucleotides in which case they will be cleaved by enzymes that are site-specific nucleases. Linkers formed from polypeptides are cleaved by peptidases.

There are many types of site-specific nucleases that may be used to cleave oligonucleotide sequences. Examples of the site-specific nucleases include restriction endonucleases, homing endonucleases, zinc finger nucleases, transcription activator-like effect in nucleases (TALONs), or clustered regularly interspaced short palindromic repeats (CRISPR)/Cas complexes. Each of these types of site-specific nucleases are well known to those having ordinary skill in the art.

Restriction enzymes (restriction endonucleases) are present in many species and are capable of sequence-specific binding to DNA (at a target or recognition site), and cleaving DNA at or near the site of binding. Over 3000 restriction enzymes have been studied in detail, and more than 600 of these are available commercially. All types of restriction enzymes recognize specific short DNA sequences and carry out the endonucleolytic cleavage of DNA to give specific fragments with terminal 5'-phosphates.

Homing endonucleases (HEs), which are also known as meganucleases, are a collection of double-stranded DNases that have large, asymmetric recognition sites (12-40 bp and coding sequences that are usually embedded in either introns or inteins. Introns are spliced out of precursor RNAs, while inteins are spliced out of precursor proteins. Unlike restriction endonucleases, HEs tolerate some sequence degeneracy within their recognition sequence. Thus, single base changes do not abolish cleavage but reduce its efficiency to variable extents. As a result, their observed sequence specificity is typically in the range of 10-12 bp.

Zinc finger nucleases (ZFNs) are synthetic proteins consisting of an engineered zinc finger DNA-binding domain fused to the cleavage domain of the FokI restriction endonuclease. ZFNs consist of a DNA-binding zinc finger domain (composed of three to six fingers) covalently linked to the non-specific DNA cleavage domain of the bacterial FokI restriction endonuclease. ZFNs can bind as dimers to their target DNA sites, with each monomer using its zinc finger domain to recognize a half-site. Dimerization of ZFNs is mediated by the FokI cleavage domain which cleaves within a five or six nucleotide "spacer" sequence that separates the two inverted "half sites."

TALENs are restriction enzymes that can be engineered to cut specific sequences of DNA. They are made by fusing a TAL effector DNA-binding domain to a DNA cleavage domain (i.e., a nuclease which cuts DNA strands). Transcription activator-like effectors (TALEs) can be engineered to bind practically any desired DNA sequence, so when combined with a nuclease, DNA can be cut at specific locations.

In the CRISPR/Cas nuclease system, the CRISPR locus encodes RNA components of the system, and the Cas (CRISPR-associated) locus, encodes proteins. CRISPR loci in microbial hosts contain a combination of CRISPR-associated (Cas) genes as well as non-coding RNA elements capable of programming the specificity of the CRISPR-mediated polynucleotide cleavage.

The Type II CRISPR is one of the most well-characterized systems and carries out targeted double-stranded breaks in four sequential steps. First, two non-coding RNAs, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. In engineered CRISPR/Cas9 systems, gRNA also called single-guide RNA ("sgRNA") may replace crRNA and tracrRNA with a single RNA construct that includes the protospacer element and a linker loop sequence.

Cas9 mediates cleavage of target DNA to create a DSB within the protospacer. Activity of the CRISPR/Cas system in nature comprises three steps: (i) insertion of alien DNA sequences into the CRISPR array to prevent future attacks, in a process called 'adaptation,' (ii) expression of the relevant proteins, as well as expression and processing of the array, followed by (iii) RNA-mediated interference with the alien polynucleotide. The alien polynucleotides come from viruses attaching the bacterial cell. Thus, in the bacterial cell, several of the so-called 'Cas' proteins are involved with the natural function of the CRISPR/Cas system and serve roles in functions such as insertion of the alien DNA, etc.

CRISPR may also function with nucleases other than Cas9. Two genes from the Cpf1 family contain a RuvC-like endonuclease domain, but they lack Cas9's second HNH endonuclease domain. Cpf1 cleaves DNA in a staggered pattern and requires only one RNA rather than the two (tracrRNA and crRNA) needed by Cas9 for cleavage. Cpf1's preferred PAM is 5'-TTN, differing from that of Cas9 (3'-NGG) in both genomic location and GC-content. Mature crRNAs for Cpf1-mediated cleavage are 42-44 nucleotides in length, about the same size as Cas9's, but with the direct repeat preceding the spacer rather than following it. The Cpf1 crRNA is also much simpler in structure than Cas9's; only a short stem-loop structure in the direct repeat region is necessary for cleavage of a target. Cpf1 also does not require an additional tracrRNA. Whereas Cas9 generates blunt ends 3 bp upstream of the PAM site, Cpf1 cleaves in a staggered fashion, creating a five nucleotide 5' overhang 18-23 bp away from the PAM.

Other CRISPR-associated proteins besides Cas9 may be used instead of Cas9. For example, CRISPR-associated protein 1 (Cas1) is one of the two universally conserved proteins found in the CRISPR prokaryotic immune defense system. Cas1 is a metal-dependent DNA-specific endonuclease that produces double-stranded DNA fragments. Cast forms a stable complex with the other universally conserved CRISPR-associated protein, Cas2, which is part of spacer acquisition for CRISPR systems.

There are also CRISPR/Cas9 variants that do not use a PAM sequence such as NgAgo. NgAgo functions with a 24-nucleotide ssDNA guide and is believed to cut 8-11 nucleotides from the start of this sequence. The ssDNA is loaded as the protein folds and cannot be swapped to a different guide unless the temperature is increased to non-physiological 55° C. A few nucleotides in the target DNA are removed near the cut site.

Peptidases or proteases are catalytically active proteins (enzymes) that cleave peptide bonds in proteins and peptides by hydrolysis. There are six catalytic types (serine, cysteine, threonine, aspartic, glutamic, and metallo). Peptidases can be classified by sequence similarities into approximately 250 families, and these can be arranged into approximately 60 clans by comparing tertiary structures. In an implementation, the protease or peptidase is an exoprotease or an exopeptidase. In an implementation, the protease or peptidase is an endoprotease or endopeptidase. The protease or peptidase may include trypsin, chymotrypsin, pepsin, papain any cathepsin (e.g., cathepsin B, L, D, K, or G). A skilled artisan will recognize that methods for the enzymatic digestion of polypeptides are well known in the art.

The enzymatically-cleavable linkers may be attached to the surface of the substrate 102 during a surface coating or functionalization step. Additionally or alternatively, the oligonucleotides or polypeptides that form an enzymatically-cleavable linker may be synthesized in situ directly onto the surface of the substrate 102. Oligonucleotide linkers are generally single-stranded DNA. However, most site-specific nucleases recognize double-stranded DNA. Therefore, cleavage of an oligonucleotide linker may include contacting the linker with a short primer sequence that hybridizes and forms a double-stranded oligonucleotide. This double-stranded region is then recognized by a site-specific nuclease. Upon cleavage of a recognition site, the oligonucleotide linker and the primer are released.

For example, a surface linker 104 that is a DNA strand with the nucleotide base sequence GAATTC will be contacted with a primer that has the reverse-complementary nucleotide base sequence of CTTAAG. In an implementation, this will be performed by flowing an excess of primers across the surface of the substrate 102 so that hybridization occurs for all surface linkers 104 having the complementary nucleotide base sequence. In this example, a restriction enzyme within cleave the double-stranded DNA (dsDNA) between the guanine and adenine bases. This would then release the polymer chain 106 with the sequence AATTC attached to the anchored monomer 110. The complementary portion of the primer, the TTAAG sequence, may remain hybridized to the portion of the surface linker 104 that is attached to the anchored monomer 110 or it may disassociate depending on changes in conditions such as temperature and salt concentration.

If an enzymatically-cleavable surface linker 104 is formed from the same monomers as the polymer chain 106, there is a possibility that the enzyme which cleaves the surface linker 104 may also cleave a portion of the polymer chain 106. To avoid this, the recognition sequence in the surface linker 104 may be selected to be different from any sequences found in the polymer chain 106. Alternatively, the sequences of the polymer chains 106 may be designed to not include any sequences that are recognized by enzymes used for cutting any of the surface linkers 104 attached to the substrate 102.

For oligonucleotide surface linkers 104 attached to oligonucleotides, existing design techniques and software for avoiding primer collisions may be adapted to identify oligonucleotide sequences for the surface linkers 104 that are not found in any of the attached polymer chains 106. If the surface linker 104 and the polymer chain 106 are polypeptides, then the surface linker 104 may be designed to include a sequence that is not present in any of the polypeptide chains using techniques similar to that for avoiding DNA primer collision.

The surface linker 104 may also be created with unnatural or modified bases to create a unique recognition site that will not be present in any of the attached polymer chains 106. For example, oligonucleotides forming the surface linker 104 may be methylated so that a restriction enzyme that only acts on methylated DNA will not cleave portions of the polymer chain 106 even if the sequence of nucleotide bases is the same as the surface linker 104. Type IIM restriction endonucleases, such as DpnI, recognize and cut only methylated DNA. The recognition site for DpnI is $G_m A | TC$ which is also referred to as the dam sequence since it is recognized by dam methylase. DpnI does not cleave unmethylated DNA and will cleave hemimethylated DNA (with only one adenine methylated) 60-fold more slowly than fully adenomethylated recognition sequences.

Alternatively, the polymer chain 106 may be created with unnatural or modified bases such as methylated bases to prevent cleavage of oligonucleotides in the polymer chain 106 by a site-specific nuclease that cleaves the surface linker 104. Methylation may be applied selectively to the polymer chain 106 to those regions of DNA that have the same nucleotide base sequence as the surface linker 104. A methyltransferase may be used to methylated all or portions of the polymer chain 106 after it has been synthesized or methylated bases may be incorporated into the polymer chain 106 as the oligonucleotide is growing.

The substrate 102 may be a two-dimensional substrate such as an array or a three-dimensional substrate such as a bead or microsphere. Arrays may be formed from silicon chips, glass, an insoluble polymer, or other material. A glass substrate 102 may be formed from controlled porous glass (CPG) with pore sizes between about 50 and 300 nm. A silica substrate has a relatively homogeneous chemical surface echoing modified using well-developed silanization chemistry. Beads may be formed from silicon, glass, polystyrene, polymeric resins, latex, etc. Magnetic beads may also be used in which magnetic material such as ferrite crystals are included in suspension of styrene/divinylbenzene monomers. The magnetic properties provide additional handling and manipulation options for magnetic beads.

The substrate 102 may be modified or functionalized prior to attachment of the surface linker 104. For example, the substrate 102 may be silanized by covering the surface of the substrate 102 with organofunctional alkoxysilane molecules. This treatment creates a uniform layer of primary amines or epoxides that are available to react with the surface linker 104. Mineral components like glass and metal oxide surfaces can all be silanized because they contain hydroxyl groups which attack and displace the alkoxy groups on the silane thus forming a covalent —Si—O—Si— bond. Modifications of the surface of the substrate 102 that provide a location for covalent coupling include the addition of carboxylic acid groups, primary aliphatic amines, aromatic amines, chloromethyl (vinyl benzyl chloride), secondary amine groups, hydrazide groups, aldehydes, hydroxyl groups, thiol groups, epoxy groups, mercaptosilanes, etc.

In an implementation, the substrate 102 may include multiple spatially-addressable electrodes. Each electrode may be independently addressable allowing the creation of arbitrary and variable voltage microenvironments across the surface of the array. This type of substrate 102 may be referred to as a "microelectrode array." The microelectrode density may be approximately 1000 microelectrodes/cm$^2$, approximately 10,000 microelectrodes/cm$^2$, or a different density. One example of a microelectrode array is provided in Bo Bi et al., *Building Addressable Libraries: The Use of "Safety-Catch" Linkers on Microelectrode Arrays,* 132 J. Am. Chem. Soc. 17,405 (2010).

Oxidation of an electrolyte solution after the application of current to microelectrodes liberates acid at the anodes; concomitant reduction at the cathodes consumes acid. In an implementation, the cathode is a palladium cathode. The ions and radicals generated by these redox reactions at the electrode surfaces move away from the electrodes and to the substrate through a combination of diffusion, migration and convection effects. During this transit time the electrode products may further react. Once the primary or secondary products reach the substrate, they may either react to remove the protecting group 116 by cleaving a chain linker 114 or liberating the polymer chain 116 from the substrate 102 by cleaving the surface linker 104. One illustrative type of bond that can be cleaved by a redox reaction is an ester that forms a carbonyl group.

The electrodes in a microelectrode array may be implemented using complementary metal-oxide-semiconductor (CMOS) integrated circuits. CMOS circuits use a combination of p-type and n-type metal-oxide-semiconductor field-effect transistor (MOSFETs) to implement logic gates and other digital circuits. Although CMOS logic can be implemented with discrete devices for demonstrations, commercial CMOS products are integrated circuits composed of up to billions of transistors of both types, on a rectangular piece of silicon of between 10 and 400 mm$^2$. A series of controllable gates/transistors implemented with CMOS circuits can be controlled to inject charge at any location on the substrate 102.

Protecting group 116 may be any type of protecting group used in organic synthesis. See, e.g., Greene et al., *Protective Groups in Organic Synthesis,* 3rd Ed., John Wiley & Sons, Inc., New York, N.Y. (1999). Protecting groups are often used to prevent a particular functional group or part of a molecule (e.g., a phosphite, a phosphate, an amine, a carboxylic acid, a thiol, a hydroxyl, a heterocycle, etc.) from reacting under certain reaction conditions (e.g., a chemical reaction in which an unprotected part of the same molecule undergoes a synthetic transformation). Hydroxyl-protecting groups are among the most commonly used protecting groups in organic synthesis. It will be appreciated that the protecting group 116 should be chosen based on the type of substituent that is protected, the structure of the molecule for which the protecting group 116 is used, the reaction conditions used, the type of solvent used, the conditions required for removing the protecting group, and the like. One of skill in the art may choose from among different protecting groups to protect functional groups. Reaction conditions that influence the choice of protecting group can typically include the pH, the temperature, the relative reactivities of the reactants and/or products, and the like.

Protecting groups for hydroxyls can include, for example, silyl ethers (e.g., trimethyl silyl, triethyl silyl, tert-butyldimethyl silyl, tert-butyldiphenylsilyl, dimethylphenylsilyl, and diphenylmethylsilyl), benzyl carbonates, trityl, monomethoxytrityl, dimethoxytrityl, esters (e.g., acetate, benzoate, and the like), pixyl, tert-butyloxycarbonyl, a tetrahydropyranyl group, photolabile protecting groups and the like. When the hydroxyl is a sugar hydroxyl, suitable protecting groups can include, for example, pixyl, acetyl, t-butyldimethylsilyl (CBDMS), trityl, monomethoxytrityl ("MMT" or "MMTr"), dimethoxytrityl ("DMT" or "DMTr"), and the like. Protecting groups for nitrogen include, for example, amides (e.g., trifluoroacetyl, acetyl, phenoxyacetyl, benzoyl, and isobutyryl), carbamates (e.g., tert-butyloxycarbonyl, (4-nitrophenyl)ethyloxycarbonyl, and N-benzyloxycarbonyl), trityl, amidines and the like.

Two protecting groups used in organic synthesis are Fmoc and Boc. Fmoc is a base-labile protecting group used in organic synthesis. Fmoc carbamate is frequently used as a protecting group for amines, where the Fmoc group can be introduced by reacting the amine with fluorenylmethyloxycarbonyl chloride (Fmoc-Cl). Another method for introducing the Fmoc group is through 9-fluorenylmethylsuccinimidyl carbonate (Fmoc-OSu), which may itself be obtained by the reaction of Fmoc-Cl with the dicyclohexylammonium salt of N-hydroxysuccinimide Fmoc may be cleaved by bases typically in a solution of piperidine or in tetra-n-butylammonium fluoride in the presence of dimethylformamide.

Boc can be used in the protection of amines and amino acids under either aqueous or anhydrous conditions, by reaction with a base and the anhydride Boc$_2$O. Active esters and other derivatives such as Boc-ONH$_2$ and Boc-N$_3$ can also be used. The Boc group is stable towards most nucleophiles and bases. tert-Butyl carbamates are cleaved under anhydrous acidic conditions with the production of tert-butyl cations. Scavengers such as thiophenol may prevent nucleophilic substrates from being alkylated. Removal of the BOC in amino acids can be accomplished with strong acids such as TFA (neat or in dichloromethane) or with HCl in methanol.

The protecting group 116 may also protect the terminal monomer 112 from addition of subsequent monomers 108 by steric hindrance. Thus, the steric bulk of the protecting group 116 rather than its chemistry may prevent polymerization reactions such as the formation of phosphodiester bonds in DNA synthesis or peptide bonds in polypeptide synthesis. Steric hindrance result from repulsive forces between overlapping electron clouds.

Figure 2:
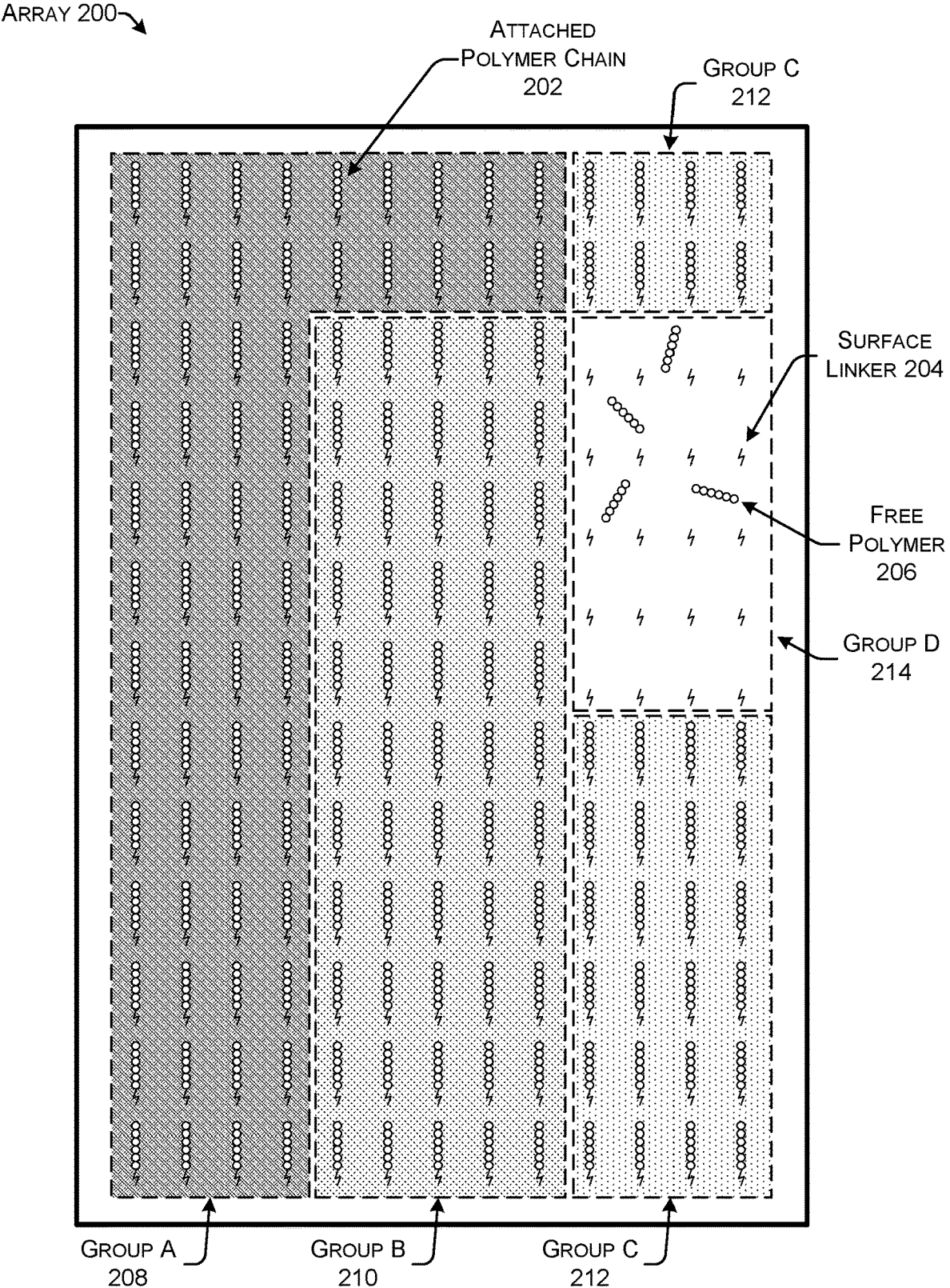
FIG. 2 illustrates an array with attached polymers belonging to separate groups.

FIG. 2 shows an array 200 partially covered with attached polymer chains 202. The attached polymer chains 202 are each attached to the array 200 by a surface linker 204. Upon cleavage of the surface linker 204, the respective polymer from the attached polymer chain 202 is released and becomes a free polymer 206. The polymer chain 202 and the surface linker 204 may be the same or similar to the polymer chain 106 and the surface linker 101 introduced in FIG. 1. Depending on the size of the array 200 and the density with which the attached polymer chain 202 are present, the array 200 may be covered with millions or billions of individual surface linkers 204 and attached polymer chains 202.

The attached polymer chain 202 may be associated with one or more different groups. The groupings may be spatial or logical based on the content of the attached polymers. Spatial groupings are based on the location of placement on the surface of the array 200. Spatial groupings may be contiguous or discontinuous and take any possible shape. For example, spatial groupings may be in a checkerboard pattern, a square, a rectangle, a circle etc. Logical groupings are based on a common feature possessed by the polymers that are grouped together. For example, if the attached polymer chains 202 are used to store digital information, the logical groupings may be based on the content of the information stored. In an implementation, all of the attached polymer chains 202 storing a portion of the digital information from the same computer file may be grouped together. Logical groupings may, but need not necessarily, share a spatial grouping. For example, all of the attached polymer chains 202 that belonged to a given logical grouping may be placed together in a contiguous spatial grouping such as a rectangle-shaped grouping. However, logical groupings need not have any defined spatial grouping. Logical groupings may be distributed randomly or pseudo-randomly across the surface of the array 200.

In this illustration, the attached polymer chains 202 are shown as being divided into four different groups: group A 208, group B 210, group C 212, and group D 214. However, in an actual implementation the number groups may be fewer or greater such as many thousands or hundreds of thousands of separate groups. Group D 214 illustrates selective cleavage of the surface linkers 204 to release the polymers in group D 214 without releasing the polymers from any of the other groups. The surface linkers 204 for each group may be cleaved separately from the surface linkers 204 of the other groups. Thus, the surface linkers 204 for any of group A 208, group B 210, group C 212, or group D 214 may be separately and independently cleaved. Group A 208, group B 210, group C 212, and group D 214 may represent either spatial or logical groupings. Spatial and logical groupings may also be combined on the same array 200. For example, group B 210 may represent a spatial grouping while group C 212 may represent a logical grouping.

Each grouping of attached polymer chains 202 may be, but is not necessarily, contiguous. For example, group C 212 is split across two separate regions. Any group may be split into any number of regions limited only by the resolution with which the surface linkers 204 are able to be selectively cleaved.

Cleavage of the surface linkers 204 may be by any of the mechanisms discussed above such as electrochemical cleavage, thermal cleavage, photocleavage, chemical cleavage, or enzymatic cleavage. If the array 200 is implemented as a microelectrode array, activation of specific sets of spatially-addressable electrodes on the microelectrode array can implement selective release of one or more groups of attached polymer chains 202. In this implementation, all of the surface linkers 204 may have the same structure and the selective activation is controlled by the microelectrodes within the array 200. The array 200, when implemented as a microelectrode array, is coupled to a power source for powering the electrodes and to control circuitry for directing the current to specified ones of the spatially-addressable electrodes. In an implementation, array 200 may be implemented with CMOS circuitry.

A microelectrode array may also implement selective cleavage of thermally-labile linkers. Electrodes in the microelectrode array may be coupled to localized heat sources such as spatially-addressable resistors. Heat created by the resistor can cleave thermally-labile linkers within sufficient proximity to the resistor that the temperature of the linker rises above its cleavage temperature. The resolution of the array 200 may be determined by the thermal properties of the array 200 itself and of any solution covering the surface of the array 200. Thus, thermal diffusion may cause surface linkers 204 that are not directly above a given spatially-addressable resistor to also cleave.

Thermally-labile linkers may be cleaved by heat sources other than resistors. For example, lasers or focused ultrasound beams may be used to heat specific portions of the array 200.

Photolabile linkers attached to the array 200 may be selectively cleaved by controlling exposure to a light source. For example, UV light directed through a photolithographic mask will irradiate and cleave only those surface linkers 204 that are exposed to the UV light. Thus, the shape of a photolithographic mask can control which group of attached polymer chains 202 are released. With photolabile linkers, all of the surface linkers 204 may have the same configuration and the control of cleavage is implemented by controlling exposure to light. In addition to use of a photolithographic mask, exposure to light may also be controlled by using a focus light sources such as a laser or array of light emitting diodes (LEDs) that directs light only on to specified portions of the array 200.

Chemically-labile linkers generally cleaved across an entire array 200 when the array is exposed to the appropriate chemical for cleaving the surface linkers 204. However, selective application of the chemical cleaving agent to some portions of the array 200 may be used to implement selective control of chemically-labile linkers. Instead of applying a chemical cleaving agent across an entire array 200 or collection of beads, the chemical cleaving agent may be applied to only selected areas by a spatially-controlled application technique. The chemical cleaving agent may be applied to the array 200 by location-specific printing such as inkjet-like printing. Chemical inkjet printing uses techniques similar to conventional printing to place nanoliter volumes of reagents at specified locations on a two-dimensional surface. The appropriate acid, base, or other chemical cleaving agent may be applied to specific surface linkers 204 by use of inkjet printing. This provides site-specific cleavage of surface linkers 204 and release of attached polymer chains 202 at the location where the reagent is dispensed.

Any type of chemical inkjet printing may be adapted for use with this disclosure. Inkjet printing can be divided into two categories: (1) drop-on-demand (DoD) or impulse inkjet, where droplets are generated when required; and (2) continuous inkjet, in which droplets are deflected from a continuous stream to a substrate when needed. Inkjet printing can be further subdivided according to the specific means of generating droplets, such as piezoelectric, thermal and electrostatic. Droplet size involves, typically, volumes ranging from 1.5 pL to 5 nL at a rate of 0-25 kHz for drop-on-demand printers (and up to 1 MHz for continuous printheads).

Electrohydrodynamic jet printing (EHJP) is another printing technology that may be used. EHJP is a high-resolution printing technology where the printed liquid is driven by an electric field. Exposure to an electric field causes mobile ions in a polarizable liquid to accumulate at the liquid surface. Deposited droplets can be as small as 240 nm with spatial accuracy in the hundreds of nm, which is typically an order of magnitude smaller than other inkjet printing technologies. Such small droplet sizes dispense less material with more spatial control, which allows for more selectivity in controlling the cleavage of specific surface linkers 204.

Enzymatically-cleavable linkers have cleavage specificity built into the sequence of the linkers (i.e., the oligonucleotide or polypeptide chain that is the linker). Thus, controlling the cleavage of enzymatically-cleavable linkers is done not by changing the local environment around the surface linkers 204, but by contacting the surface linkers 204 with the appropriate enzyme. Thus, during design construction of the array 200, all polymers that belong to the same group are attached to the array 200 by surface linkers 204 that have the same sequence or a similar sequence that is cleaved by the same enzyme. Different groups such as group A 208, group B 210, group C 212, and group D 214 may be differentiated by use of surface linkers 204 that have sequences which are recognized by different enzymes. Those of ordinary skill in the art will appreciate that design of the enzymatically-cleavable linkers for different groups on the same array 200 will consider cross-reactivity and select linker sequences that are not cleaved by any of the enzymes used for cleaving linkers of the other groups.

Preventing cross-reactivity between surface linkers 204 used with different groups may also be achieved by using different types of enzymatically-cleavable linkers. For example, a first group of polymers could be attached to the array 200 by oligonucleotides that are cleaved by a restriction endonuclease and a second group of polymers could be attached to the array 200 by polypeptides that are cleaved by a peptidase. The use of different types of polymers for the enzymatically-cleavable linkers (i.e., oligonucleotides and polypeptides) provides orthogonality between these two sets of surface linkers 204.

Figure 3:
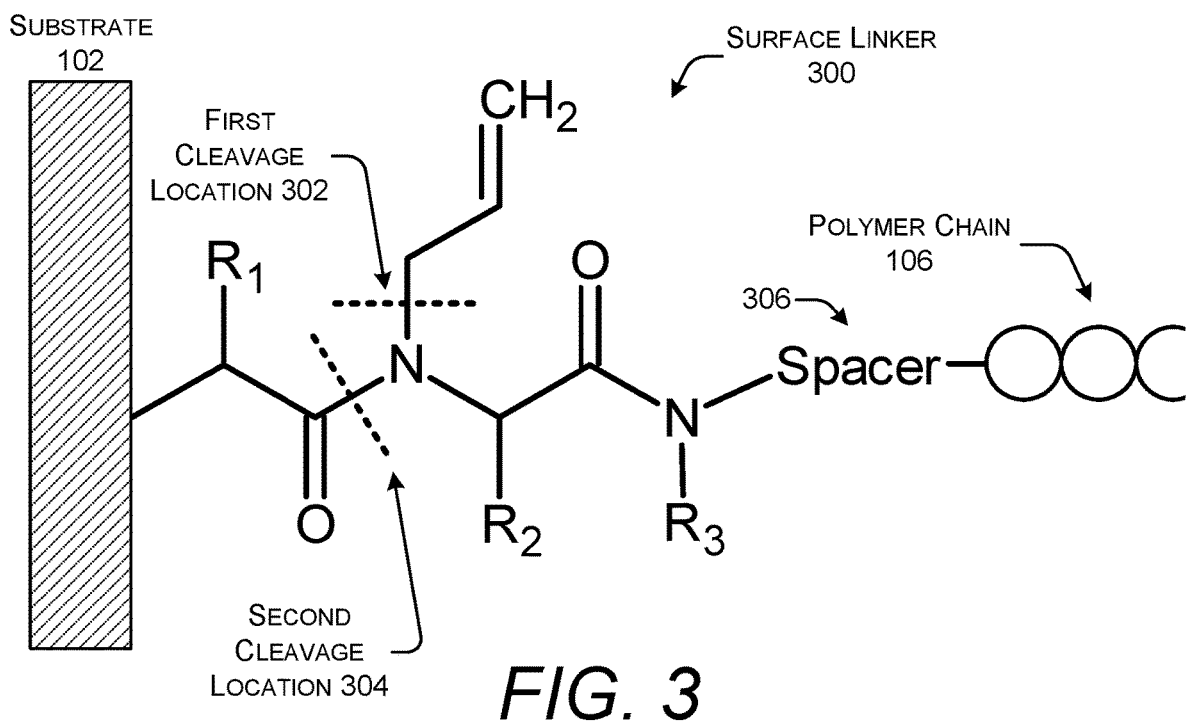
FIG. 3 illustrates an implementation of a surface linker.

FIG. 3 shows an illustrative surface linker 300 that may be attached to the substrate 102. $R_1$ and $R_2$ are independently selected amino acid side chains that include one or more amino acids. This polypeptide chain may be synthesized using conventional solid-state peptide synthesis techniques. $R_3$ is hydrogen (H) or an allyl group ($H_2C=CH-CH_2-$). This surface linker 300 uses a two-stage cleavage process. Two-stage cleavable linkers are not limited to the specific structure shown in FIG. 3 but include any linker structure that has a first cleavable group which protects a second cleavable group from cleavage. The first cleavable group may be attached by a first cleavage location 302 which in an implementation is an electrochemically cleavable bond that may be cleaved by oxidation caused by activating a spatially-addressable electrode on a microelectrode array. Cleavage of the second cleavable group cleaves the surface linker 300 and releases any bound polymer from the substrate 102. The second cleavable group may be any group that reacts to a different cleavage trigger than the first cleavable group. In an implementation, the second cleavage location 304 is a peptide bond that is cleaved by peptidase which recognizes the sequence of polypeptides extending from $R_1$ through $R_2$. A peptide bond is an amide type of covalent chemical bond linking two consecutive alpha-amino acids from C1 (carbon number one) of one alpha-amino acid and N2 (nitrogen number two) of another along a polypeptide or protein chain.

The surface linker 300 may also include a spacer 306. The spacer 306 may be an organic spacer (e.g., an aliphatic spacer, an alkyl spacer, an aromatic spacer, an alkylene glycol, a polyethylene glycol, a carbohydrate (e.g., a sugar)), or the like. In an implementation, the spacer 306 may be a PEG spacer. PEG spacers are well-known inert spacers used in many biotechnological applications. If the spacer 306 is omitted, a functional group on the polymer chain 106 may connect directly to the nitrogen on the surface linker 300.

Removal of the allyl group by cleavage at the first cleavage location 302 exposes the peptide bond to the peptidase. Electrochemical control of the first cleavage location 302 allows for site-specific cleavage of the surface linker 300. When contacted by the peptidase after cleavage at the first cleavage location 302, the peptidase cleaves at the second cleavage location 304 and release the polymer chain 106. However, the peptidase only cleaves those surface linkers 300 for which the protecting allyl group was removed. Thus, even if the peptidase is applied uniformly across the surface of an array covered with surface linkers that have identical structures, only those surface linkers 300 for which cleavage has occurred at the first cleavage location 302 will be cleaved by the peptidase.

Cleavage of the polypeptide chain at the second cleavage location 304 leaves a scar attached to the polymer chain 106. The scar includes the spacer 306 and the peptide of polypeptides that make up $R_2$. If necessary, the scar may be removed through subsequent processing of the polymer chain 106.

In an implementation, an array such as the array 200 introducing FIG. 2 may be covered with the surface linker 300. Cleavage of individual ones of the surface linker 300 may be selectively controlled by activating specific electrodes in the array 200.

Figure 4:
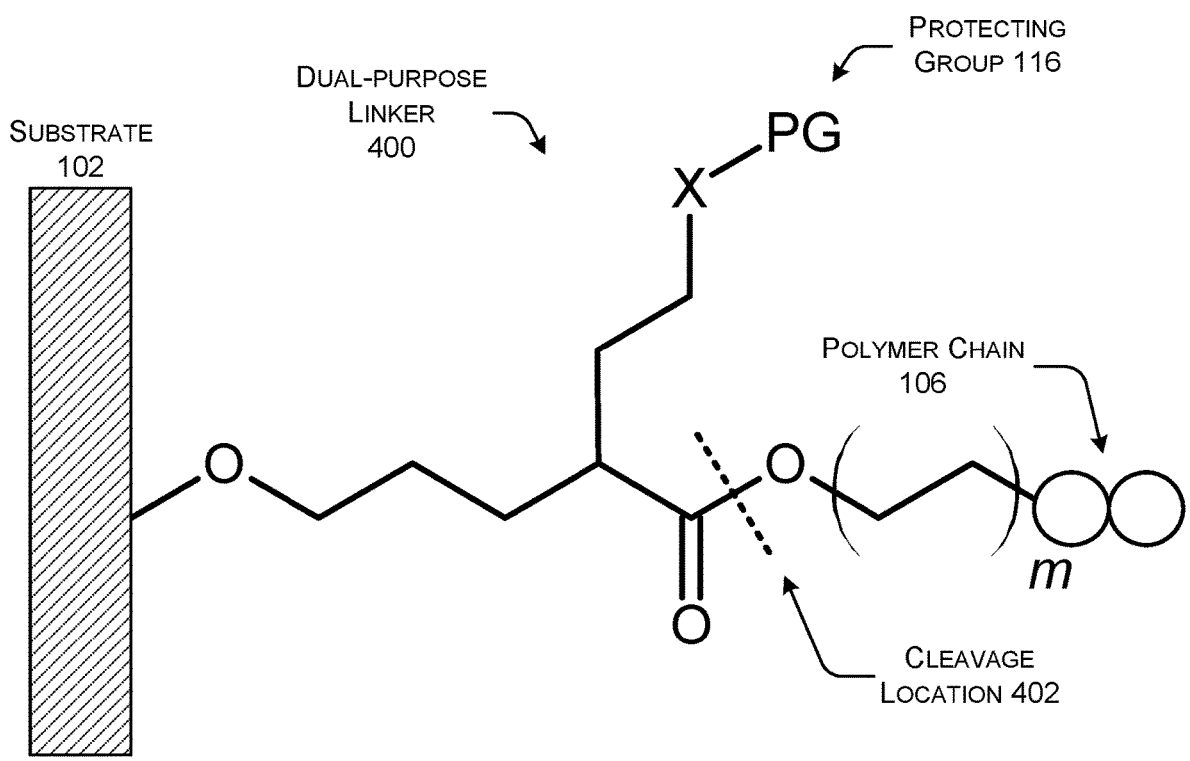
FIG. 4 illustrates an implementation of a linker that is a surface linker or a chain linker.

FIG. 4 shows a dual-purpose linker 400 that in implementations may function as either a surface linker or a chain linker. The dual-purpose linker 400 may include an alkoxy bond to the substrate 102 if functioning as a surface linker. When functioning as a surface linker, the dual-purpose linker 400 may omit the side chain that contains the protecting group 116. The cleavage location 402 is in an ester that is connected to the polymer chain 106 by a variable length hydrocarbon chain (m represents the number of ethylene units in the hydrocarbon chain).

If functioning as a chain linker, the dual-purpose linker 400 will include the protecting group 116. The protecting group 116 may be any of the types of protecting groups discussed above. The protecting group 116 is connected to the remainder of the dual-purpose linker 400 by a variable group X that is either oxygen (O) or a secondary amine (N—H). When functioning as a chain linker, the dual-purpose linker 400 will lack a covalent connection to the substrate 102. Thus, instead of an alkoxy bond to the substrate 102, the dual-purpose linker 400 may end with a hydroxyl group. Alternatively, the sidechain between the ester and the substrate 102 may be truncated or omitted.

The cleavage location 402 may be cleaved by exposure to electrons created by an electrode such as an electrode on a microelectrode array (e.g., microelectrode away 200).

Figure 5:
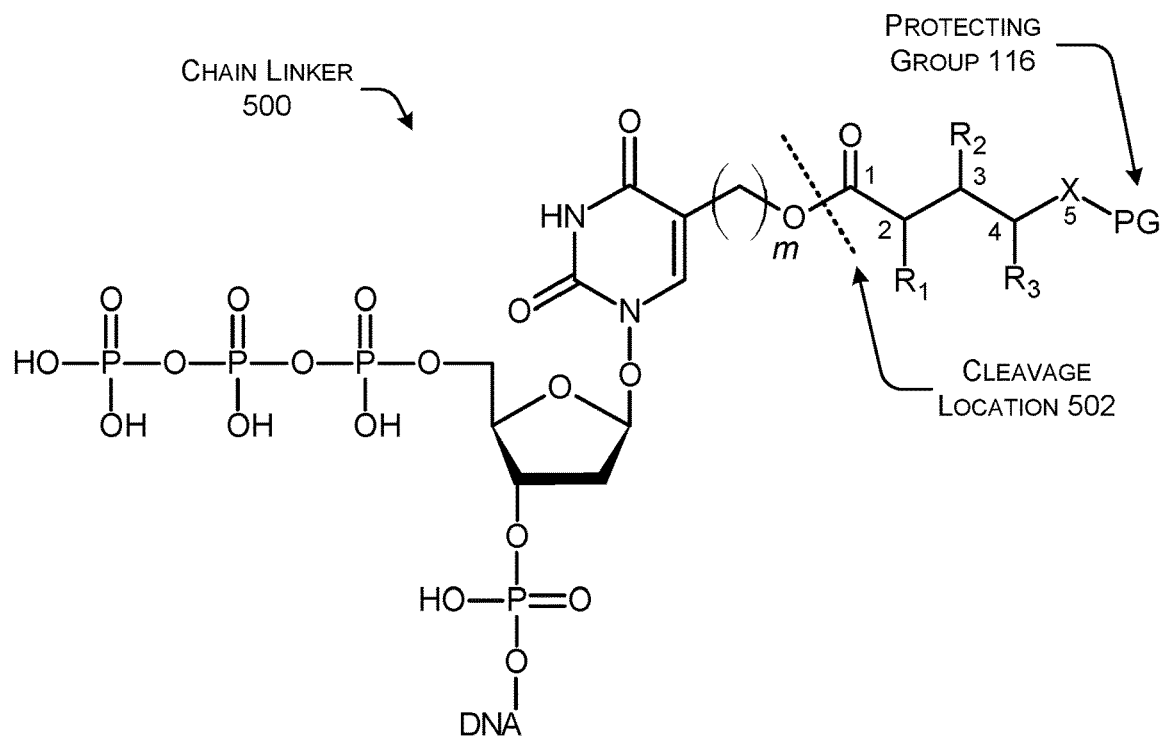
FIG. 5 illustrates an implementation of a chain linker.

FIG. 5 shows a chain linker 500 use for adding a protecting group 116 onto the growing strand of DNA. The chain linker 500 includes a deoxy nucleotide triphosphate. Chain linker 500 is illustrated with the pyrimidine base cytosine; however, the other pyrimidine bases uracil or thiamine may be substituted. The protecting group 116 may be any of the protecting groups described previously. In one implementation, the protecting group 116 may be benzonitrile. Removal of the protecting group 116 triggers cleavage of the chain linker 500 at cleavage location 502.

The protecting group 116 is connected to the pyrimidine base by a variable length sidechain where m represents one or more carbon atoms (C). A hydrocarbon connector connects the ester to the protecting group 116. $R_1$, $R_2$, and $R_3$ may be the same or different and may be a saturated alkyl contain from about one to about 10 carbon atoms. The term "saturated alkyl" means a straight- or branched-chain saturated alkyl. Examples of saturated alkyls include methyl, ethyl, propyl, isopropyl, n-butyl, sec-butyl, octadecyl, and the like. One of $R_1$, $R_2$, and $R_3$ includes a DNA polymerase optionally attached via a spacer such as any of the type of spacers described in conjunction with spacer 306 of FIG. 3. Thus, in this implementation the enzyme that catalyzes growth of the oligonucleotide chain is covalently attached to a nucleotide monomer. A variable group X is either oxygen (O) or a secondary amine (N—H).

The DNA polymerase may be any type of DNA polymerase that can extend the growing oligonucleotide chain. In an implementation, the DNA polymerase attached at one of $R_1$, $R_2$, or $R_3$ may be terminal deoxynucleotidyl transferase (TdT), also known as DNA nucleotidylexotransferase (DNTT) or terminal transferase. TdT catalyzes the addition of nucleotides to the 3' terminus of a DNA molecule. Unlike most DNA polymerases, it does not require a template. The preferred substrate of this enzyme is a 3'-overhang, but it can also add nucleotides to blunt or recessed 3' ends. Cobalt is a cofactor, however, TdT catalyzes polymerization upon Mg and Mn administration in vitro.

The cleavage location 502 is an ester that is cleaved by removal of the protecting group. Activation of an electrode may cause removal of the protecting group and cleavage at the cleavage location 502. Although this cleavage location may be several oligonucleotides away from the surface of a microelectrode array it can be affected by a microelectrode in the array. Upon electrochemical activation, removal of the protecting group and cleavage at the cleavage location 502 induces a cyclization that produces a five- or six-member heterocycle including positions numbered 1 to 5. A heterocyclic compound or ring structure is a cyclic compound that has atoms of at least two different elements as members of its ring(s). This leaves a scar attached to the pyrimidine base that includes a variable length hydrocarbon chain ending with a hydroxyl group.

Figure 6:
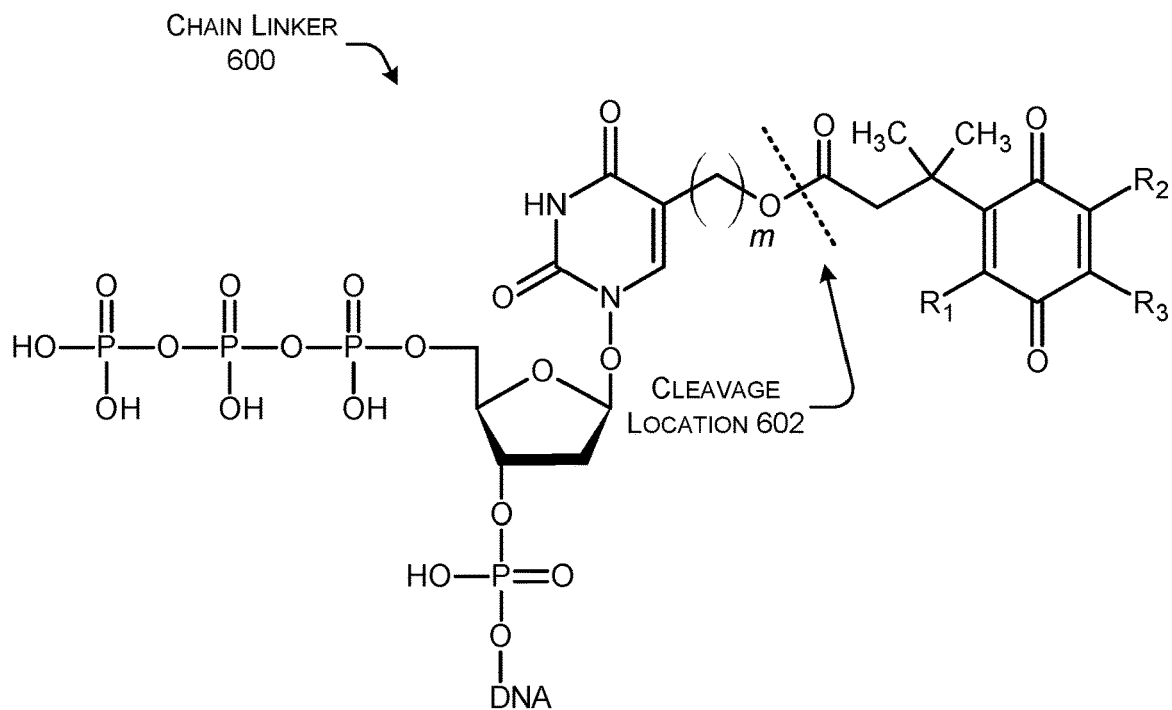
FIG. 6 illustrates an implementation of a chain linker

FIG. 6 shows a chain linker 600 with a different structure but similar functionality to the chain linker 500 shown in FIG. 5. $R_1$, $R_2$, and $R_3$ may be the same or different and may be a saturated alkyl contain from about one to about 10 carbon atoms and one of $R_1$, $R_2$, and $R_3$ includes a DNA polymerase option attached via a spacer. The cleavage location 602 is an ester that is attached to the pyrimidine base by a variable length hydrocarbon chain. Cytosine is shown as the pyrimidine base; however, any other pyrimidine base may be substituted. Cleavage of chain linker 600 at cleavage location 602 leaves a similar scar as described above for chain linker 500. The leaving group following cleavage at cleavage location 602 is a two-membered ring.

The scars left following cleavage of any of the surface linker 300, the dual-purpose linker 400, the chain linker 500, the chain linker 600, or any other linker contained in the disclosure may be removed from the polymer chain by subsequent processing. Scars attached to ssDNA strands may be removed, or more precisely diluted, by polymerase chain reaction (PCR) amplification. Copies of the ssDNA strand created by PCR amplification would be formed from nucleosides that do not have scars. Thus, none of the population of double-stranded DNA molecules created by PCR would have scars except for the molecule that incorporates the original ssDNA strand.

Illustrative Processes

For ease of understanding, the processes discussed in this disclosure are delineated as separate operations represented as independent blocks. However, these separately delineated operations should not be construed as necessarily order dependent in their performance. The order in which the processes are described is not intended to be construed as a limitation, and unless other otherwise contradicted by context any number of the described process blocks may be combined in any order to implement the process or an alternate process. Moreover, it is also possible that one or more of the provided operations is modified or omitted.

Figure 7:
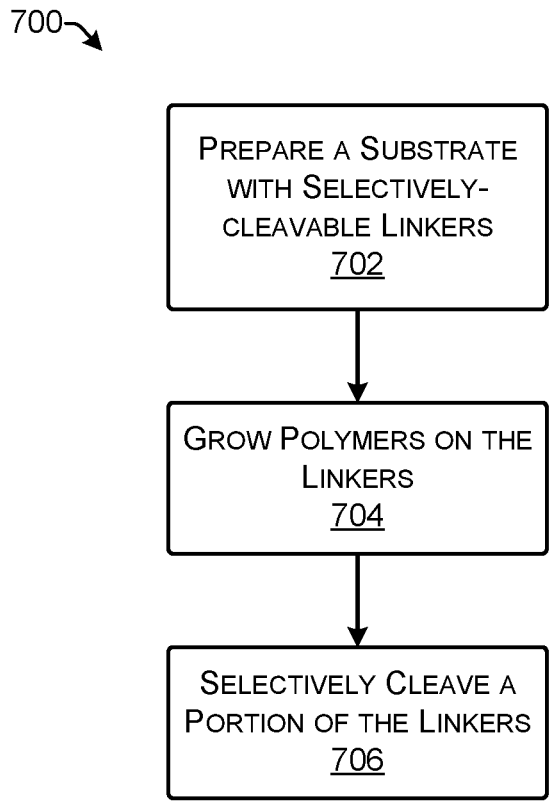
FIG. 7 is a flow diagram showing an illustrative process for selectively detaching polymers from a substrate.

FIG. 7 shows process 700 for selectively detaching polymers from a substrate by the use of selectively-cleavable linkers. Process 700 may be implemented, for example, using one of the linkers shown in FIG. 3 or FIG. 4.

At 702, a substrate is prepared with selectively-cleavable linkers. The substrate may be the same or similar to the substrate 102 introduce in FIG. 1. The selectively-cleavable linkers may be the same or similar to the surface linker 104 introduced in FIG. 1, the surface linker 204 introduced in FIG. 2, the surface linker 300 introduced in FIG. 3, or the dual-purpose linker 400 introduced FIG. 4.

The selectively-cleavable linkers may be electrochemically-cleavable linkers, photolabile linkers, thermolabile linkers, acid-labile linkers, base-labile linkers, or enzymatically-cleavable linkers. The substrate may be any of the types of substrates discussed above such as a two-dimensional array or a three-dimensional bead. Preparation of the substrate may include functionalization of the surface such as by silanization or another technique to add reactive groups such as esters or amides to the surface of the substrate. In an implementation, the surface of the substrate may be coated with agarose or another polysaccharide.

The selectively-cleavable linkers are attached to the substrate by a reaction that forms a covalent bond between the linkers and the substrate itself or coating on the substrate. In an implementation, linkers may be attached to the substrate by an ester or amide linkage. Techniques for attaching linkers to substrates, such as ester chemistry for attaching the linker to a surface, are well-known to those having ordinary skill in the art. Known techniques for solid phase synthesis of oligonucleotides or polypeptides may be adapted for attachment of any of the linkers described in this disclosure.

The selectively-cleavable linkers attached to the substrate may all be the same (i.e., a large number of beads all coated with the same linkers) or a single substrate may be coated with two or more different types of linkers. For example, an array may be coated with a first enzymatically-cleavable linker with a recognition site for a first enzyme on a first portion of the array and a second enzymatic-cleavable linker with a recognition site for a second enzyme on a second portion of the array.

At 704, polymers are grown on the selectively-cleavable linkers attached to the substrate. The polymers may be the same or similar to the polymer chain 106 introduced in FIG. 1. For example, the polymers may be oligonucleotides grown by conventional solid-phase oligonucleotide synthesis techniques or polypeptides grown by conventional solid-phase peptide synthesis techniques. Techniques for growing oligonucleotides include synthesis that proceeds in the 5' to 3' direction as well as in the 3' to 5' direction.

At 706, a portion of the linkers are selectively cleaved. Selective cleaving of the linkers cleaves some but not all of the linkers on the substrate. The linkers to be selectively cleaved, and thus the polymers that will be released may be selected after synthesis by changing local conditions on a portion of the substrate.

The local conditions may be changed by activating one or more spatially-addressable electrodes on the substrate. Activating the electrodes may oxidize the linkers resulting in cleavage of covalent bonds separating the attached polymer from the substrate. Activating spatially-addressable resistors creates heat at the locations of the activated resistors. The heat can cleave thermolabile linkers in the proximity of the activated resistors. Controlled application of light to the substrate such as with optoelectronics or by applying light through a lithographic photomask can change local conditions by directing the light onto only selected portions of the substrate. The wavelength of the light may be selected to be a wavelength that cleaves the photolabile linkers.

Chemically-labile linkers may also be cleaved by selectively applying appropriate chemical cleaving agents to only portions of the substrate. For example, acid-labile linkers may be cleaved by selectively applying acid to only those portions of the substrate for which cleavage is desired. Similarly, base may be selectively applied to cleave base-labile linkers. Techniques for control application of limited volumes of chemical cleaving agents include chemical inkjet printing to place small volumes of the cleaving agents at specific positions on the surface of a two-dimensional array. Thus, the acid or the base may be selectively applied to portions of the substrate without applying acid or base to other portions of the substrate. These are examples of directly mediated cleavage.

Another technique for changing local conditions to induce cleavage of acid-liable linkers or base-labile linkers is to selectively apply light to activate a photoacid generator or a photobase generator. This is an example of indirectly mediated cleavage. Light may be applied to a portion of the substrate using any of the techniques suitable for photolabile linkers. The selective application of light limits the portions of the substrate in which acid is generated by a photoacid generator or in which base is generated by a photobase generator. Accordingly, the chemically-labile linkers are cleaved only on the portions of the substrate that receive light. Examples of photobase generators include carbamates, O-acyloximes, and ammonium salts. See e.g., Kanji Sugiyama and Masamitsu Shirai, *Photobase generators: Recent progress in application trend in polymer systems*, 34(2) Progress in Polymer Sci. 194 (2009). Examples of photoacid generators include designs based on ionic, benzyl ester, imino ester, spiropyran, and terarylene frameworks. See e.g., Collin Martin et al., *Recent progress in development of photoacid generators*, 34 J. of Biochemistry and Photobiology C: Photochemistry Reviews 41 (2018).

Selective cleavage of a portion of the linkers may be performed to release only those polymers that share a logical relationship. For example, if the polymers are oligonucleotides including digital information, selective cleavage of the linkers may be used to release only those polymers that include digital information from the same computer file. The substrate could then be washed by removing only the oligonucleotides that include digital information for the specific computer file. These oligonucleotides may be stored together such as in a container such as an Eppendorf tube or dried onto a substrate such as filter paper. Thus, oligonucleotides that encode digital information from the same computer file are able to be stored together without contamination from oligonucleotides containing digital information for other computer files. This process could be repeated to isolate and separately store multiple groups oligonucleotides each group encoding digital information from a different computer file.

Selective cleavage of enzymatically-cleavable linkers is performed by selection of the enzyme used to cleave the linkers. If a substrate is covered with two or more sets of selectively-cleavable linkers that are cleaved by different enzymes (e.g., two sets of oligonucleotide linkers that have different recognition sequences or a set of oligonucleotide linkers cleaved by a restriction endonuclease and a set of polypeptide linkers cleaved by a peptidase) then selecting an enzyme based on the recognition sequence of the linkers to be cleaved will result in cleavage of only the selected subset of linkers. Thus, the grouping of linkers and the resolution with which different polypeptides can be separated from the substrate is based on the choice of linkers used at 702 when the substrate is prepared.

Figure 8:
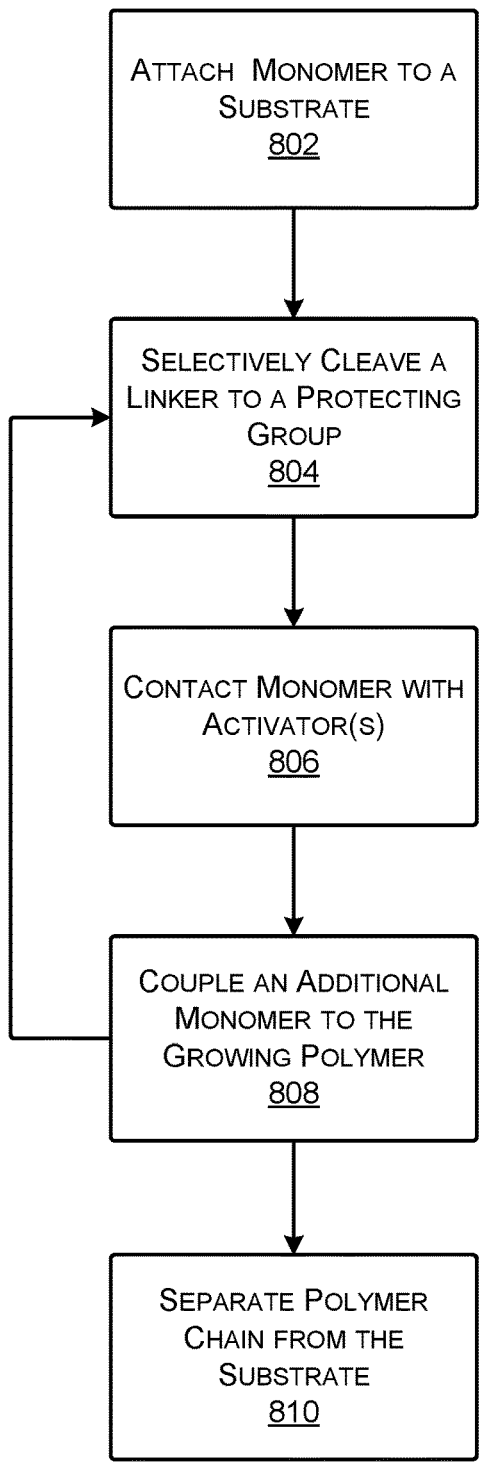
FIG. 8 is a flow diagram showing an illustrative process for controlling growth of a polymer with a protecting group attached by a selectively-cleavable linker

FIG. 8 shows process 800 for controlling the growth of a polymer using a protecting group that is attached with a selectively-cleavable linker. Process 800 may be implemented, for example, using one of the linkers shown in FIG. 4, FIG. 5, or FIG. 6.

At 802, a monomer is attached to a substrate. The monomer may be the same or similar to the anchoring monomer 110 introduced in FIG. 1. The substrate may be the same or similar to the substrate 102 also introduced in FIG. 1. In some implementations, the monomer may be a nucleotide or an amino acid anchored to the substrate using conventional solid phase oligonucleotide synthesis or solid phase peptide synthesis techniques. Alternatively, the monomer may be anchored to the substrate using a selectively-cleavable linker as described in this disclosure.

At 804, a linker to protecting group is selectively cleaved. The protecting group prevents extension of the polymer chain. The protecting group may be any of the types of protecting groups described elsewhere in this disclosure. The linker may be the same or similar to the chain linker 114 and the protecting group may be the same or similar to the protecting group 116 introduced in FIG. 1. In implementations, the protecting group may be any protecting group used with conventional oligonucleotide synthesis (e.g., 5'-DMT (4,4'-dimethoxytrityl) or peptide synthesis techniques (e.g., Fmoc or Boc).

Cleavage of the linker and removal of the protecting group exposes the monomer attached to the substrate so that an additional monomer may be added to extend a growing polymer chain. Oligonucleotide synthesis may begin with either a template ssDNA or with a linker. Synthesis can proceed in the 5' to 3' direction or, depending on specific synthesis technique, in the 3' to 5' direction. Thus, the linker may be attached to either the 5' or the 3' hydroxyl groups of a dNTP. Natural dNTPs containing the protecting group are incorporated into the growing chain using transferase enzymes such as TdT. The protecting group itself may be covalently attached to the enzyme that polymerizes the monomers such as in implementations in which the TdT enzyme is attached to dNTPs by a linker. The protecting group on the dNTP prevents multiple incorporation of that same base onto the growing polymer chain. Removal of the printing group may be referred to as a "deblock step."

At 806, the monomer may be contacted with one or more types of activators. For example, in phosphoramidite synthesis of oligonucleotides, the diisopropylamino group of the incoming phosphoramidite monomer in the solvent acetonitrile is 'activated' (protonated) by the acidic catalyst ETT (5-(ethylthio)-1H-tetrazole). Synthesis of peptides can also use activators. Amide bond formation between an amine and carboxylic acid is slow, and as such usually requires "coupling reagents" or activators. Activation of the carboxyl group generally involves the formation of an "active ester" in situ. Activators for peptide synthesis may be Carbodiimides such as dicyclohexylcarbodiimide (DCC) and diisopropylcarbodiimide (DIC). Alternatively, aminium/uronium or phosphonium salt of a non-nucleophilic anion (tetrafluoroborate or hexafluorophosphate) may be used as activators for peptide synthesis. Examples of aminium/uronium reagents include HATU (HOAt), HBTU/TBTU (HOBt) and HCTU (6-C1HOBt). HBTU and TBTU differ only in the choice of anion. Phosphonium reagents include PyBOP (HOBt) and PyAOP (HOAt).

At 808, an additional monomer is coupled to the growing polymer. Once the protecting group is removed, the polymer chain is available for addition of the next monomer. Any type of polymerization technique, such as by chemical or enzymatic methods, may be used to add an additional monomer on to the final monomer on the growing polymer chain (e.g., the terminal monomer 112 shown in FIG. 1). Reactive groups on any or all of the monomers in the polymer chain may be protected by additional protecting groups that have a different cleavage mechanism than the protecting group that prevents extension of the polymer chain. The additional monomer added onto the growing polymer chain may also include a protecting group attached by a chain linker. Thus, the protecting group prevents multiple incorporation of the same monomer onto the growing polymer chain.

Process 800 may proceed iteratively from 808 and return to 804 where the protecting group is removed by cleavage of a linker and polymer extension continues.

At 810, upon completion of synthesis of the polymer, the polymer chain may be separated from the substrate by cleaving a surface linker using any of the selectively-controllable or conventional cleavage techniques described in this disclosure. Prior to separation from the substrate or following separation from the substrate, protecting groups on any reactive groups of the monomers of the polymer chain may be removed.

If separation of the polymer chain from the substrate is implemented by cleavage of selectively-cleavable linkers such as the surface linker 104, the surface linker 300, the dual-purpose linker 400, or another linker, individual polymers are groups of polymers may be released while synthesis continues for other polymers. Assuming orthogonality between the linkers attaching the polymer chain to the substrate and the linkers attaching a protecting group that prevents further polymerization, continuation of polymerization and release of a polymer from the substrate may be controlled independently.

Furthermore, depending on specific linker chemistry, surface linkers that have been cleaved to release bound polymers may be reused to start synthesis of a new polymer. For example, the surface linkers 204 for group D 214 in FIG. 2 may be reused after selective release of the attached polymer chains. This particular while polymer synthesis is ongoing for one or more of the other groups on array 200.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A method of site-specific cleavage of attached polymers from a substrate, the method comprising: preparing the substrate with selectively-cleavable linkers; growing polymers on the selectively-cleavable linkers; and selectively cleaving a portion of the selectively-cleavable linkers by changing local conditions on a portion of the substrate thereby releasing polymers attached to the portion of the substrate.

Clause 2. The method of clause 1, wherein the selectively-cleavable linkers comprise electrochemically-cleavable linkers and the substrate comprises spatially-addressable electrodes.

Clause 3. The method of any of clauses 1-2, wherein the selectively-cleavable linkers comprise photolabile linkers and the local conditions comprise light contacting the photolabile linkers.

Clause 4. The method of any of clauses 1-3, wherein the selectively-cleavable linkers comprise thermolabile linkers and the substrate comprises spatially-addressable resistors.

Clause 5. The method of any of clauses 1-4, wherein the selectively-cleavable linkers comprise acid-labile linkers or base-labile linkers and selectively cleaving a portion of the selectively-cleavable linkers comprises selectively applying acid or base to the portion of the substrate without applying acid or base to other portions of the substrate.

Clause 6. The method of clause 5, wherein selectively applying acid or base to the portion of the substrate comprises location-specific printing of the acid or the base onto the portion of the substrate.

Clause 7. The method of any of clauses 1-6, wherein the selectively-cleavable linkers are two-stage cleavable linkers comprising a first cleavable group that, when removed, exposes a second cleavable group that attaches the polymers to the substrate.

Clause 8. The method of any of clauses 1-7, wherein the polymers comprise oligonucleotides or polypeptides.

Clause 9. An article of manufacture comprising: a substrate comprising an array of independently-addressable electrodes; a surface linker bound to the substrate in proximity to an electrode of the array, the surface linker comprising at least one chemical bond that cleaves in response to activation of the electrode; and a polymer attached to the surface linker.

Clause 10. The article of manufacture of clause 9, wherein the substrate comprises complementary metal-oxide-semiconductor integrated circuits.

Clause 11. The article of manufacture of any of clauses 9-10, wherein the at least one chemical bond comprises a bond in an ester connected to an alkoxy group.

Clause 12. The article of manufacture of any of clauses 9-11, wherein the surface linker comprises an amino acid sequence that becomes accessible to a peptidase upon cleavage of the at least one chemical bond.

Clause 13. The article of manufacture of clause 12, wherein the at least one chemical bond comprises a bond between a nitrogen of a peptide bond and an allyl group.

Clause 14. The article of manufacture of any of clauses 9-13, wherein the surface linker comprises a thermolabile linker and the independently addressable electrodes are coupled to resistors configured to generate heat.

Clause 15. The article of manufacture of any of clauses 9-14, wherein the polymer comprises an oligonucleotide having a sequence that encodes digital information.

Clause 16. A selectively-cleavable chain linker comprising: an attachment to a monomer of a polymer chain; a protecting group that prevents extension of the polymer chain or protects a side group of the monomer from reacting; and a bond cleaved by a redox reaction upon addition of electrons.

Clause 17. The selectively-cleavable chain linker of clause 16, wherein the monomer comprises a nucleotide or an amino acid.

Clause 18. The selectively-cleavable chain linker of any of clauses 16-17, wherein the protecting group is selected from the group comprising acetyl, carbamate, benzyl, benzoyl, Boc, and Fmoc.

Clause 19. The selectively-cleavable chain linker of any of clauses 16-18, wherein the protecting group prevents extension of the polymer chain due to steric hindrance.

Clause 20. The selectively-cleavable chain linker of any of clauses 16-19, further comprising a covalently-attached enzyme that polymerizes the monomer into the polymer chain.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

The invention claimed is:

1. A selectively-cleavable two-stage surface linker comprising:
    a point of attachment to a substrate;
    a first amide bond;
    a second amide bond;
    an allyl group connected to the nitrogen of the first amide bond; and
    a point of attachment to a polymer chain, wherein the polymer chain is an oligonucleotide or a polymer other than a polypeptide;
    wherein, the linker is configured such that cleavage at a first cleavage location separates the allyl group from the nitrogen of the first amide bond exposes a second cleavage location that is the first amide bond to cleavage by a peptidase.

2. The selectively-cleavable two-stage surface linker of claim 1, further comprising a spacer between the second amide bond and the polymer chain.

3. The selectively-cleavable two-stage surface linker of claim 2, wherein the spacer comprises an aliphatic spacer, an alkyl spacer, an aromatic spacer, an alkylene glycol, a polyethylene glycol, a carbohydrate, or a PEG spacer.

4. The selectively-cleavable two-stage surface linker of claim 1, further comprising a first side chain between the first amide bond and the point of attachment to the substrate, wherein the first side chain comprising one or more amino acid side chains.

5. The selectively-cleavable two-stage surface linker of claim 1, further comprising a second side chain between the first amide bond and the second amide bond, wherein the second side chain comprising one or more amino acid side chains.

6. The selectively-cleavable two-stage surface linker of claim 1, further comprising a third side chain from the nitrogen of the second amide bond, wherein the third side chain is a hydrogen or an allyl group.

7. The selectively-cleavable two-stage surface linker of claim 1, having the following structure:

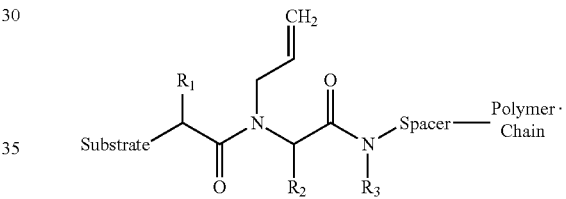

wherein $R_1$, $R_2$, and $R_3$ are all independently organic groups comprising at least one hydrogen.

8. The selectively-cleavable two-stage surface linker of claim 7, wherein $R_1$ and $R_2$ are both independently one or more amino acid side chains and $R_3$ is hydrogen or an allyl group.

9. The selectively-cleavable two-stage surface linker of claim 1, wherein the polymer chain is an oligonucleotide.

* * * * *